US006488633B1

(12) United States Patent
Schnall (10) Patent No.: US 6,488,633 B1
(45) Date of Patent: Dec. 3, 2002

(54) PROBE DEVICES PARTICULARLY USEFUL FOR NON-INVASIVE DETECTION OF MEDICAL CONDITIONS

(75) Inventor: Robert P. Schnall, Kiryat Bialik (IL)

(73) Assignee: Itamar Medical (C.M.) Ltd., Ceasarea (IL)

(*) Notice: Subject to any disclaimer, the term of this patent is extended or adjusted under 35 U.S.C. 154(b) by 0 days.

(21) Appl. No.: 09/499,354

(22) Filed: Feb. 8, 2000

(30) Foreign Application Priority Data

Jul. 14, 1999 (IL) .................................. 130939

(51) Int. Cl.⁷ .................................. A61B 5/02
(52) U.S. Cl. .................. 600/481; 600/485; 600/499
(58) Field of Search .................. 600/481, 485–488, 600/490, 499–500

(56) References Cited

U.S. PATENT DOCUMENTS

| | | | |
|---|---|---|---|
| 3,104,661 A | 9/1963 | Halpern ..................... 128/2.05 |
| 3,920,004 A | 11/1975 | Nakayama ................. 128/2.05 |
| 4,030,485 A | 6/1977 | Warner ..................... 128/2.05 |
| 4,112,491 A | 9/1978 | Bugay ........................ 364/415 |
| 4,406,289 A | 9/1983 | Wesseling et al. .......... 128/670 |
| 4,437,470 A | 3/1984 | Prost ......................... 128/679 |
| 4,677,984 A | 7/1987 | Sramek ...................... 128/681 |
| 4,821,734 A | 4/1989 | Koshino ..................... 128/680 |
| 4,836,219 A | 6/1989 | Hobson et al. ............. 128/782 |
| 4,846,189 A | 7/1989 | Sun ............................ 128/679 |
| 4,862,895 A | 9/1989 | Yamasawa et al. ......... 128/680 |
| 4,926,867 A | 5/1990 | Kanda et al. ............... 128/633 |
| 5,065,749 A | 11/1991 | Hasebe et al. .............. 128/664 |
| 5,280,791 A | 1/1994 | Lavie ......................... 128/696 |
| 5,301,675 A | * 4/1994 | Tomita .................... 600/490 X |
| 5,337,744 A | 8/1994 | Branigan .................... 128/633 |
| 5,365,924 A | 11/1994 | Erdman ...................... 128/633 |
| 5,438,986 A | 8/1995 | Disch et al. ................ 128/633 |
| 5,542,421 A | 8/1996 | Erdman ...................... 128/633 |

FOREIGN PATENT DOCUMENTS

EP    0 465 345       1/1992
WO    WO 98/04182    2/1998

OTHER PUBLICATIONS

R. P. Schnall, N. Gavriely, S. Lewkowicz and Y. Palti, "A rapid noninvasive blood pressure measurement method for discrete value and full waveform determination," Journal of Applied Physiology, Jan. 1996, pp. 307–314.
R. P. Schnall, Abstract of Doctoral Thesis, "The Development of a New Blood Pressure Measurement Technique and its Application to the Study of the Circulation," Abstracts of Research Theses, Sep. 1991, p. 68.
R. P. Schnall, Research Thesis, "The Development of a New Blood Pressure Measurement Technique and its Application to the Study of the Circulation," Sep. 14, 1990.

(List continued on next page.)

Primary Examiner—Cary O'Connor
Assistant Examiner—Ryan Carter
(74) Attorney, Agent, or Firm—Sughrue, Mion, Zinn, Macpeak & Seas, PLLC (57) ABSTRACT

A device for application to a body part of a patient to determine the physiological condition of the patient. The device includes a housing, in the form of a hollow socket closed at its distal end and open at its proximal end, for receiving the body part, a pressurizing device for applying a pressure field around the body part when received in the housing, and a sensor for sensing changes in the body part related to changes in pulsatile blood volume therein. The housing includes at least three contiguous but separate sections including a distal end section at its distal tip, a proximal end section at its opposite end, and at least one middle section between the end sections. The pressurizing device applies a pressure field to the portions of the body part received within at least the distal end section and the middle section of the housing. The distal end section is configured to apply pressure to all of the distal portion of the body part including its distal most tip. The sensor is configured to sense pulsatile volume changes in at least one segment distal to the proximal-most segment.

31 Claims, 7 Drawing Sheets

OTHER PUBLICATIONS

C. Guilleminault, R. Stoohs, A. Clerk, M. Cetel and P. Maistros, "A Cause of Excessive Daytime Sleepiness The Upper Airway Resistance Syndrome," Chest 104, pp. 781–787 (1993).

P. L. Ludmer, A. P. Selwyn, T. L. Shook, et al., "Paradoxical Vasoconstriction Induced by Acetylcholine in Athero–sclerotic Coronary Arteries," New England Journal of Medicine, vol. 315, No. 17, pp. 1046–1051 (1986).

L. Kuo, M. J. Davis and W. M. Chilian, "Endothelium–Dependent, Flow–Induced Dilation of Isolated Coronary Arterioles," The American Physiological Society, vol. 259, pp. H1063–H1070 (1990).

D. Jain, M. Burg, R. Soufer and B. L. Zaret, "Prognostic Implications of Mental Stress–Induced Silent Left Ventricular Dysfunction in Patients with Stable Angina Pectoris," American Journal of Cardiology, vol. 76, pp. 31–35 (1995).

C. Kurata, K. Tawarahara, K. Sakata, T. Taguchi, Y. Fukumoto, A. Kobayashi et al., "Electrocardiographically and Symptomatically Silent Myocardial Ischemia During Exercise Testing," Japanese Circulation Journal, vol. 55, pp. 825–834 (1991).

M. Ishibashi, T. Yasuda, N. Tamaki and H. W. Strauss, "Evaluation of Symptomatic vs. Silent Myocardial Ischemia Using the Ambulatory Left Ventricular Function Monitor (VEST)," Israel Journal of Medical Science, vol. 25, No. 9, pp. 532–538 (1989).

W. Jiang, M. Babyak, D. S. Krantz, R. A. Waugh, R. E. Coleman, M. M. Hanson, et al., "Mental Stress–Induced Myocardial Ischemia and Cardiac Events," JAMA, vol. 275, No. 21, pp. 1651–1656 (1996).

A. Rozanski, J. A. Blumenthal and J. Kaplan, "Impact of Psychological Factors of the Pathogenesis of Cardiovascular Disease and Implications for Therapy," Circulation, pp. 2192–2217 (1999).

B. Hedblad, M. Ögren, L. Janzon, S.–O. Isacsson and S. E. Lindell, "Low pulse–wave amplitude during reactive leg hyperaemia: an independent, early marker for ischaemic heart disease and death. Results from the 21–year follow–up of the prospective cohort study 'Men born in 1914', Malmö, Sweden," J. Int. Med., vol. 236, pp. 161–168 (1994).

Chapter 23, "Air plethysmography in arterial and venous disease," Non–Invasive Diagnostic Techniques in Vascular Disease, Third edition, E. F. Bernstein (ed.), Mosby, St. Louis (1985).

Chapter 59, "The pulse volume recorder in peripheral arterial disease," Non–Invasive Diagnostic Techniques in Vascular Disease, Third edition, E. F. Bernstein (ed.), Mosby, St. Louis (1985).

C. M. Edwards, J. M. Marshall and M. Pugh, "The cutaneous vasoconstrictor response to venous stasis is normal in subjects with primary Raynaud's disease," Clin. Auton. Res., vol. 9, No. 5, pp. 255–262 (1999).

M. Ögren, B. Hedblad, S.–O. Isacsson, L. Janzon, G. Jungquist, S.–E. Lindell and P. Wollmer, "Plethysmographic pulse wave amplitude and future leg arteriosclerosis," Antherosclerosis, vol. 113, pp. 55–62 (1995).

* cited by examiner

ND BACKGROUNRRR
PROBE DEVICES PARTICULARLY USEFUL FOR NON-INVASIVE DETECTION OF MEDICAL CONDITIONS

This application claims foreign priority from Israeli Application No. 130939 filed in Israel on Jul. 14, 1999 which application is hereby incorporated by reference as if fully set forth herein.

FIELD AND BACKGROUND OF THE INVENTION

The present invention relates to probe devices which apply a predetermined static pressure to a body part of a patient, preferably a digit (i.e., a finger or toe) of the patient, while non-invasively detecting certain medical conditions. The invention is particularly useful in the methods and apparatus described in our PCT Application PCT/IL97/00249, published as International Publication No. WO98/04182 on Feb. 5, 1998, and in our Israel Application 124787 filed Jun. 7, 1998; and the invention is therefore described below with respect to such methods and apparatus.

Publication WO 98/04182 discloses methods and apparatus for the non-invasive detection of a change in a physiological condition of a patient by monitoring changes in the peripheral arterial tone as manifested by changes in the arterial blood volume in a terminal extremity of a body part, preferably a digit (finger or toe) of the patient. The method and apparatus are described therein particularly for detecting mycardial ischemia and sleep apnea, and also for continuously monitoring blood pressure. The preferred constructions described therein generally include a probe for application to the patient's body part (e.g., finger). The probe includes a housing for receiving the distal end of the patient's body part, and pressurizing means for applying a static pressure field substantially uniformly around the distal end of the patient's body part when received in the compartment, including its terminal-most extremity. The static pressure field is of a predetermined magnitude sufficient to substantially prevent distention of the venous vasculature, uncontrolled venous backflow, and retrograde shockwave propagation into the distal end of the body part, and to partially unload the wall tension of, but not to occlude, the arteries in the distal end of the body part when at heart level or below. The probe further includes a sensor for sensing changes in the distal end of the patient's body part related to changes in volume therein which are due to changes in instantaneous blood volume related to arterial tone.

Publication WO 98/04182 discloses various types of devices or probes which may be used, and many applications of such devices. Some of the devices measure changes in volume in the distal end of the digit accompanying blood pressure waves, while other devices measure changes in optical density in the distal end of the digit accompanying blood pressure waves.

Further information concerning the construction and operation of such devices, as well as many of the applications in which such devices may be used, appears in our Publication WO 98/04182, which is hereby incorporated herein by reference.

It was found that at times the sensors used in such devices were extremely sensitive to movements of the finger, such as finger jitter during exercise. Such movements of the finger tend to produce volume changes which could affect the accuracy of the sensor in detecting the change in the actual physiological condition of the patient being monitored.

OBJECTS AND BRIEF SUMMARY OF THE PRESENT INVENTION

An object of the present invention is to provide a device for application to a body part of a patient to detect a change in the physiological condition of the patient, which device exhibits less sensitivity to movements of the body part during its use. Another object of the invention is to provide a device of the foregoing type which is of a relatively simple construction, and which therefore can be produced in volume and at relatively low cost.

According to the present invention, there is provided a device for application to a body part of a patient to detect a change in the physiological condition of the patient, comprising: a housing for receiving the body part; pressurizing means for applying a pressure field around the body part when received in the housing; and a sensor for sensing changes in the body part related to changes in blood volume therein; characterized in that: the housing includes at least three contiguous but separate sections including a distal end section at its distal tip, a proximal end section at its opposite end, and at least one middle section between the end sections; and in that the pressurizing means applies a pressure field to the portions of the body part received within at least the distal end section and the middle section of the housing; and the sensor senses changes in the portion of the body part received within the middle section of the housing.

In most of the preferred embodiments of the invention described below, the pressurizing means also applies a pressure field to the proximal end section and comprises one or more deformable membranes, preferably of resilient elastomeric material, within the housing defining a separate fluid chamber within each housing section; and a fluid pressure source for applying a fluid pressure, preferably a static fluid pressure, to all the chambers.

According to further features in these preferred embodiments of the invention described below, the housing is configured to receive a digit of the patient and includes: a closed distal end, enclosing one or more chambers, for receiving the distal end of the patient's digit; and an open proximal end, enclosing one or more additional chambers, at the opposite end of the housing and connected thereto by the middle section.

As will be described more particularly below, a device constructed in accordance with the foregoing features is less sensitive to certain movements of the patient's body part, (e.g., a finger), during the test period. This is because the sensor measurements are taken in the area of the middle chamber which is open at both ends, and therefore longitudinal movements of the finger, (e.g., finger jitter during exercise) would tend to produce substantially equal movements at the two ends of the middle section, such that the effects of such movements on the sensor measurements taken in the middle chamber tend to cancel each other.

In one described embodiment, the housing is constituted of a plurality of parts secured together, and the chambers are also constituted of separate membranes, one secured within each of the parts. In a second described embodiment, the housing is constituted of a single part of tubular shape, and the chambers are also constituted of a single membrane of tubular shape, the device including a plurality of internal annular rings for pressing spaced annular portions of the membrane to the inner surface of the housing to define the separate fluid chambers within the housing.

A third embodiment is also described below wherein the closed distal end of the housing, and the end fluid chamber therein, are of substantially shorter length than the other portions of the housing and the fluid chambers therein. In addition, the end fluid chamber in the closed distal end section of the housing includes an abutment element having a concave surface for receiving the distal tip of the patient's digit.

A fourth embodiment is also described below, wherein the housing is in the shape of a cylinder open at both ends, and the distal end is closed by a fluid chamber mounted therein. In one variation of this embodiment, only the fluid chamber closes the distal end of the cylinder; whereas in another variation the end fluid chamber closing the open end of the cylinder includes a rigid element mounted within the distal end of the cylinder and enclosed by the membrane defining the end fluid chamber. In the construction wherein the rigid element is enclosed by the membrane, the rigid element is formed with holes therethrough permitting the free flow of fluid within the end chamber with respect to both sides of the rigid element.

Still further embodiments are described wherein the proximal end section includes a sponge cushion rather than a pressurized chamber.

All of the foregoing embodiments may be implemented in relatively simple structures capable of being produced in volume and at a low cost.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figures 1, 2, 3:
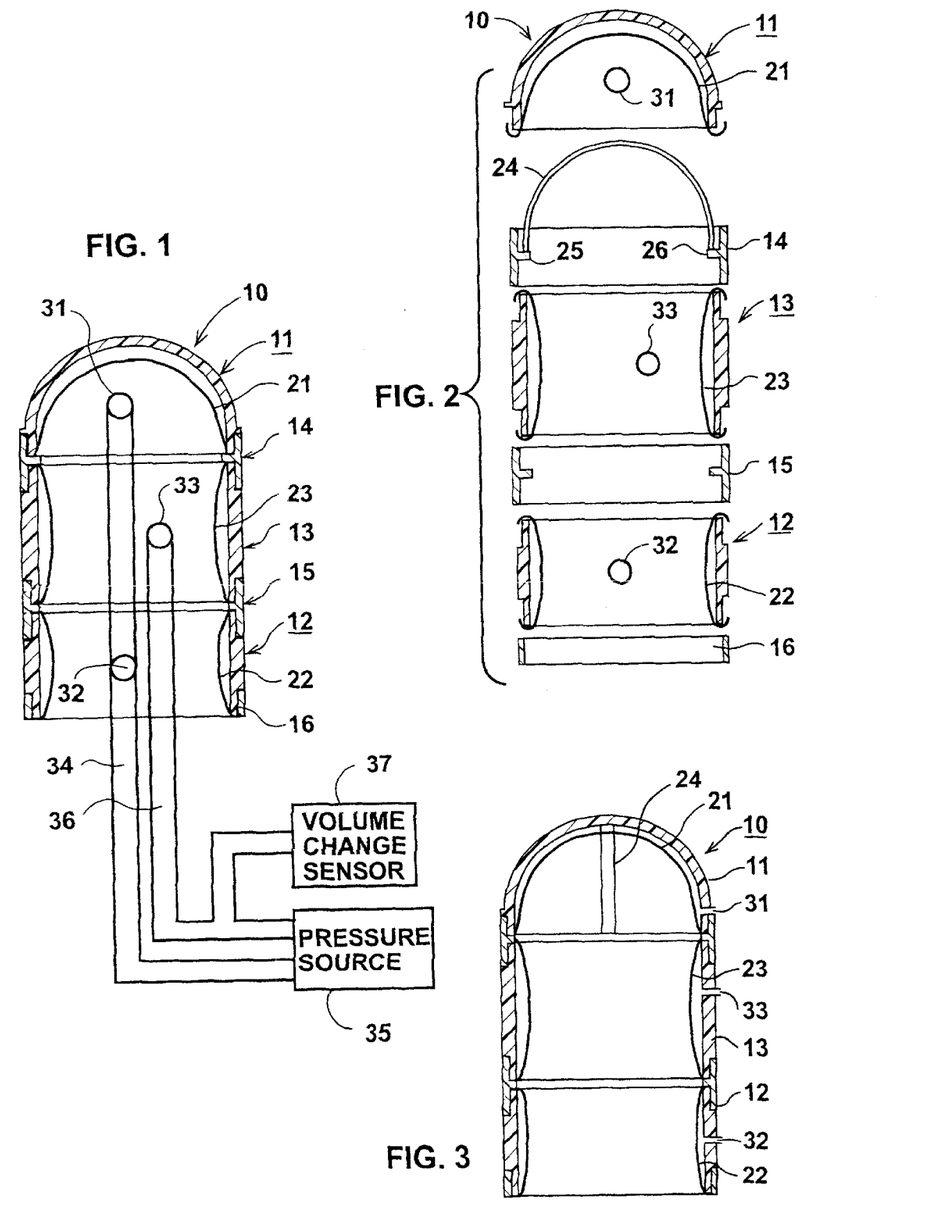
FIG. 1 illustrates one form of device including a probe constructed in accordance with the present invention for application to a finger of a patient.
FIG. 2 is an exploded view of the probe in FIG. 1.
FIG. 3 is an assembled view illustrating the probe of FIGS. 1 and 2 rotated 90°.

The Device of FIGS. 1–3

The device illustrated in FIGS. 1–3 is generally similar to those described in the above-cited Publication WO98/04182, in that it includes: a housing 10, for receiving a body part of a patient, in this case a digit (preferably a finger) of the patient, to detect certain changes in the physiological condition of the patient; pressurizing means for applying a pressure field, preferably a static, uniform pressure field, around the patient's digit when received in the housing 10; and a sensor for sensing changes in the patient's digit related to changes in blood volume therein. The pressurizing means includes a deformable membrane of elastomeric material defining one or more fluid chambers with the housing, and a pressure source for applying a static fluid pressure to the chambers.

Publication WO98/04182 discloses a number of constructions in which the housing is constituted of a single section having a single fluid chamber, or two sections each having a fluid chamber. In the two-section construction, the sensor measurements are taken from the chamber of the distal section (with respect to the patient's heart), and changes in the distal tip of the patient's digit received in that section are sensed.

An important difference in the device illustrated in FIGS. 1–3 of the present application, over those described in Publication WO98/04182, is that the housing in the device of FIGS. 1–3 includes at least three contiguous but separate sections, namely a distal end section at its distal tip 11, a proximal end section at its opposite end 12, and at least one middle section 13 between the end sections. These housing sections thus define at least three separate fluid chambers, namely one chamber within each end of the housing, and at least one chamber within the middle portion of the housing. The sensor senses changes in the portion of the patient's digit received within the chamber or chambers enclosed by the middle portion of the housing. Since this middle chamber has an end chamber on each side, and is therefore open on each side, longitudinal motions of the body part occurring during the time the test is performed (e.g., finger jitter during an exercise) tend to cancel each other, as will be described more particularly below, thereby making the device less sensitive to movements of the body part during the measurement period.

The structure of the finger probe 10 illustrated in FIGS. 1–3 is best seen in the exploded view of FIG. 2. The probe includes a rigid housing constituted of three contiguous sections, namely: a thimble-shaped cap 11 at the closed distal end of the housing; an annular collar 12 at the open proximal end of the housing; and an intermediate sleeve 13 secured between the thimble-shaped cap 11 and the annular collar 12. A first annular ring 14 secures one end of the intermediate sleeve 13 to the open end of the thimble-shaped cap 11; and a second annular ring 15 secures the opposite end of the intermediate sleeve 13 to one end of the annular collar 12. A third annular ring 16 is provided at the opposite end of the annular collar 12, constituting the proximal end of the probe housing 10 through which the patient's finger is introduced.

The three housing sections defined by parts 11, 12 and 13 enclose three separate chambers defined by three separate membranes, namely: a distal membrane 21 within the thimble-shaped cap 11 at the distal end of the housing; an annular membrane 22 within the annular collar 12 at the proximal end of the housing; and an intermediate annular membrane 23 within the intermediate sleeve 13 at the middle section of the housing.

The distal membrane 21 is also of a thimble-shape as housing part 11, and has an open end which is secured within the housing cap 11 also by annular ring 14. Annular membrane 23 within the intermediate sleeve 13 is secured at its end facing cap 11 also by ring 14, whereas its opposite end is secured by ring 15. Annular membrane 22 within the annular collar 12 is also secured at its end facing intermediate sleeve 13 by ring 15, and its opposite end is secured by ring 16.

The probe illustrated in FIGS. 1–3 is of the type which includes a substantially U-shape restraining bar, shown at 24 in FIGS. 2 and 3. As described with respect to the embodiment of FIGS. 7a and 7b in Publication WO98/04182, incorporated herein by reference in this case, the U-shaped restraining bar 24 is mounted by its legs 25, 26 to annular ring 14 to be disposed within the distal membrane 21 and to press it against inner surface of the thimble-shaped cap 11. As described in this Publication, bar 24 divides the chamber defined by that end cap into two sub-chambers to be located on opposite sides of the distal tip of the patient's digit when inserted into the probe housing 10. The provision of this restraining bar produces a two-point clamping action on the inserted finger and prevents pop-off, as well as axial and rotational movements, of the finger relative to the probe housing. Preferably, the U-shaped bar 24 is shaped so as to permit fluid communication between the two sub-chambers within that part of the probe housing. If such fluid communication is not provided for, each sub-chamber would require its own pressurizing means.

The three parts 11, 12, 13 of the probe housing 10, are each formed with an opening 31, 32, 33, respectively, providing communication with their respective fluid chambers. Openings 31 and 32 in housing parts 11 and 12 are connected by a common tube 34 to a pressure source 35 for applying a static pressure field to the fluid chambers in these two parts, constituting the distal and proximal ends, respectively, of the probe housing. Opening 33 in the intermediate sleeve 13 is connected by a separate tube 36 to the same pressure source 35, but in addition, to a volume change sensor 37, which measures change in volume within the middle section of the probe housing 10 defined by the intermediate sleeve 13.

The apparatus illustrated in FIGS. 1–3 is otherwise constructed and operates in substantially the same manner as described in Publication WO98/04182. However, since sensor 37 is associated with the fluid chamber within the intermediate sleeve 13, and since the sleeve is open at its two opposite ends, the output of sensor 37 is less sensitive to longitudinal movements of the digit during the measurement period. Thus, a longitudinal movement of the finger, in the direction of the distal tip, will tend to increase the pressure of the fluid at the distal end of the chamber enclosed within the middle housing part 12, but at the same time will tend to decrease the pressure at the proximal end of that chamber. Since the sensor (37 FIG. 1) senses total volume changes in the chamber of the probe, the two effects will tend to cancel each other, thereby reducing the net effect on the measurement obtained.

Figure 4:
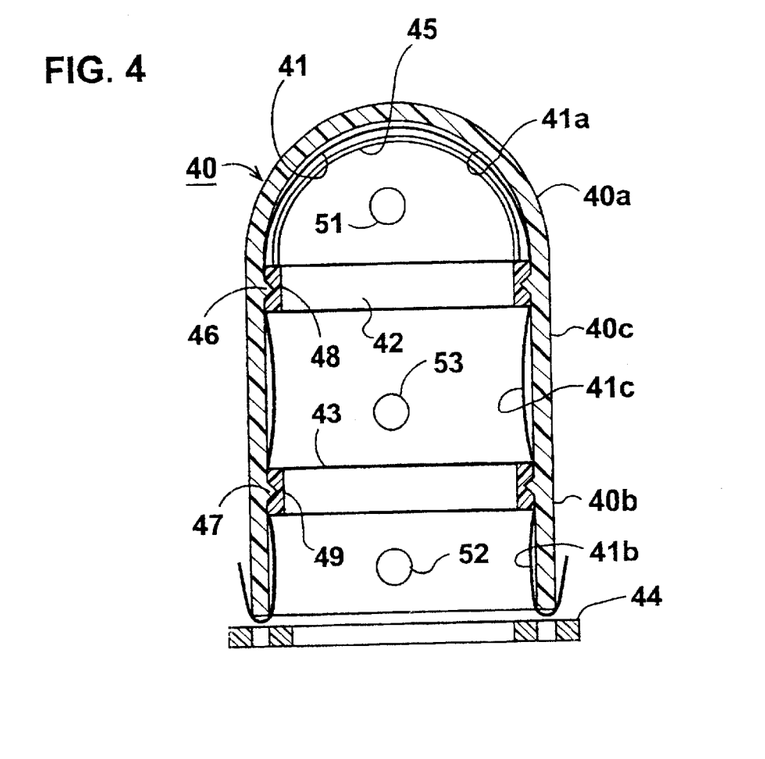
FIG. 4 illustrates another probe constructed in accordance with the present invention.
Figure 5:
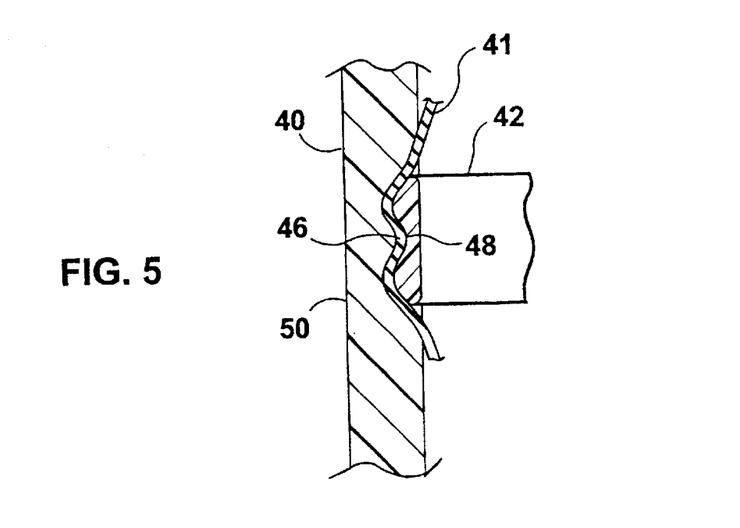
FIG. 5 is an enlarged fragmentary view more particularly illustrating the probe of FIG. 4.

The Device of FIGS. 4 and 5

FIG. 4 illustrates a probe including a housing, generally designated 40, of a one-piece construction, having a membrane 41 within it also of a one-piece construction. Both the housing 40 and the membrane 41 are of tubular shape, including a closed distal end and an open proximal end. The probe housing 40 illustrated in FIG. 4 is divided into the three segments 40a, 40b and 40c, corresponding to the three housing sections in FIGS. 1–3 by two inner annular rings 42, 43, and an outer annular ring 44 at the proximal end of the housing. The distal annular ring 42 carries the Y-bar, shown at 45, for dividing the chamber at the distal end 40a of the housing into two sub-chambers, as described above with respect to FIGS. 1–3.

The two annular rings 42, 43 are inserted into the probe housing 40 at spaced locations therein to define the three chambers within that housing. For this purpose, the inner surface of the probe housing 40 is formed with two annular ribs 46, 47, axially spaced from each other. These ribs are adapted to receive, with a snap-fit, annular recesses 48, 49 formed in the outer surfaces of the two annular rings 42, 43. Ribs 46, 47, are located such that when they receive rings 42, 43, with a snap-fit, the rings press spaced annular portions of the membrane 41 against the inner surface of the housing 40 to define the three separate fluid chambers: namely the distal chamber defined by the distal end 41a of membrane 41 with the distal end 40a of the housing 40; the proximal chamber defined by the proximal end 41b of the membrane 41 with the proximal end 40b of the housing; and the intermediate chamber defined by the middle portion 41c of the membrane with the middle portion 40c of the housing.

The inner surfaces of the annular rings 42, 43, are preferably flush with the inner surface of the housing 40 when the rings are inserted in the above manner. For this purpose, it is preferable to form each of the two annular ribs 46, 47, in an annular recess in the inner surface of the housing 40. Such a recess, having a depth substantially equal to the thickness of the respective ring 42, 43, is shown at 50 in the enlarged fragmentary view of FIG. 5. The opposite ends of the inner rings 42, 43, are preferably rounded in order to facilitate their insertion into the housing. In addition, a negative pressure may be applied between the membrane 41 and the housing 40 to facilitate the insertion of the rings.

Housing 40 is also formed with the three openings 51, 52, 53, providing communication between the three chambers, the pressure source (35 FIG. 1), and the volume change sensor (37 FIG. 1), in the same manner as described above.

Figure 6:
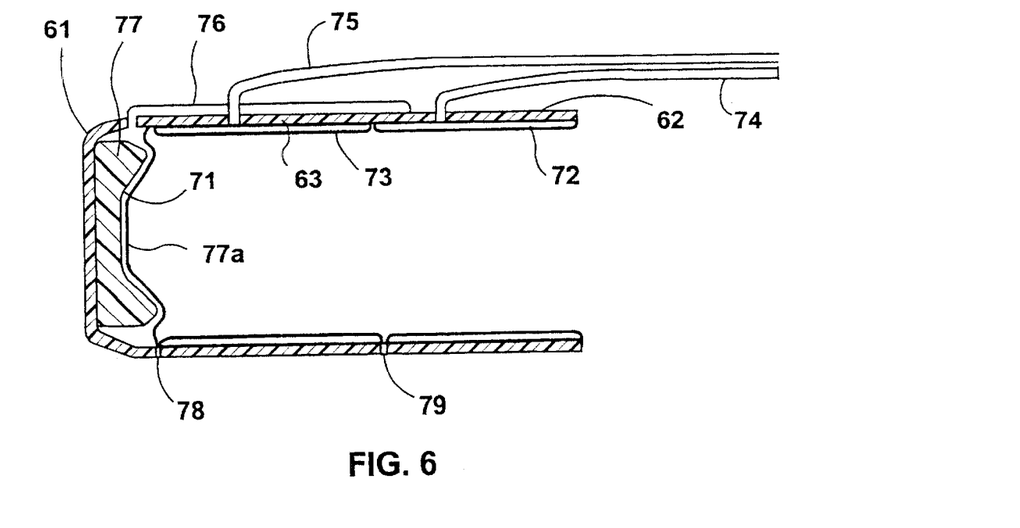
FIG. 6 illustrates another probe constructed in accordance with the present invention.
Figure 7:
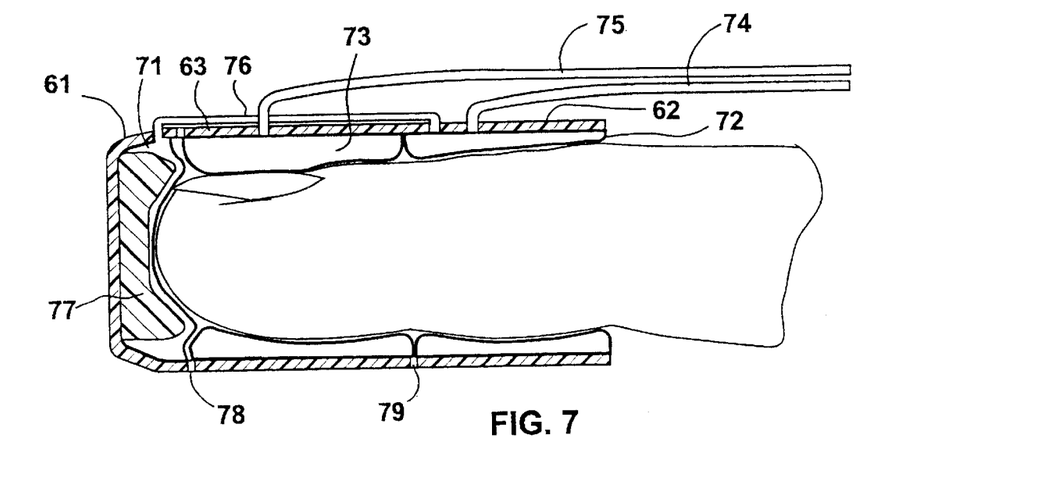
FIG. 7 illustrates the probe of FIG. 6 as applied to a finger of a patient.

The device of FIGS. 6 and 7

FIGS. 6 and 7 illustrate a probe construction wherein the closed distal end, therein designated 61, of the housing, and its end chamber 71, are of substantially shorter length than the other housing sections 62, 63, and their fluid chambers 72, 73. In such a construction as can be seen in particularly from FIG. 7, most of the end fluid chamber 71 in the closed distal end section 61 of the housing is forwardly of the distal tip of the patient's finger, and very little of that chamber envelops the finger.

In addition, a tube 74 connects the proximal chamber 72 to a pressure source, and a second tube 75 connects the intermediate chamber 73 to a volume change sensor, as described above with respect to FIGS. 1–3. In this case, however, the distal end chamber 71 is fluidly coupled to the proximal open chamber 72 by a further tube 76.

In addition, the end fluid chamber 71 in the distal end section 61 of the housing includes an abutment element 77 having a concave surface 77a for receiving the distal tip of the patient's finger when inserted into the probe. The opposite face 77b of the abutment element 77 is fixed to the end wall of the distal end section 61. This end wall could be flat (as shown), or curved, as in the constructions illustrated in FIGS. 1–4.

Since the intermediate housing section 73 and the proximal end section 72 enclose substantially the complete length of the patient's finger, with little of it being enveloped by the distal end section 61, the probe is held quite firmly on the finger even without the use of the U-bar (e.g., 24, FIGS. 2, 3), since there is little tendency for the fluid in fluid chamber 71 to push out the finger from the probe. This is particularly true if the intermediate chamber 73 is pressurized first.

A further feature presented in the probe illustrated in FIGS. 6 and 7 is the provision of air vents 78 between housing sections 61 and 63, and air vents 79 between housing sections 63 and 62. Such air vents permit any trapped air to be forced out of the probe, allowing the pressurized membranes to occupy the intervening space, and thus to improve coverage of the pressure field over the finger.

Figure 8:
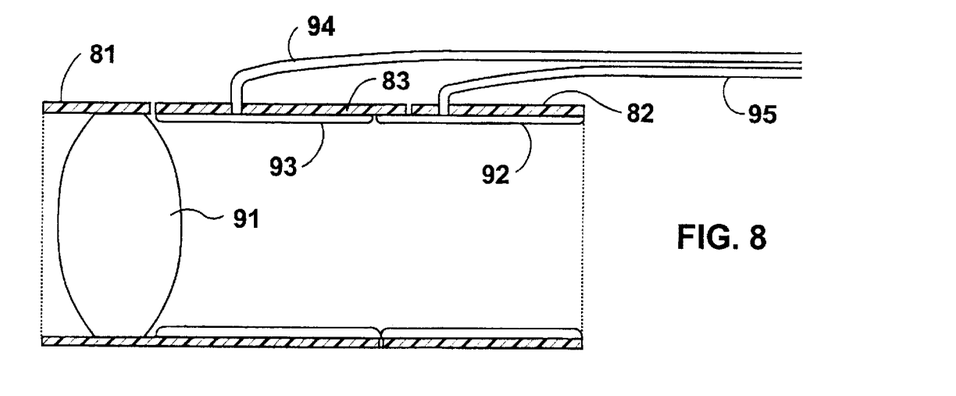
FIG. 8 illustrates another probe constructed in accordance with the present invention.
Figure 9:
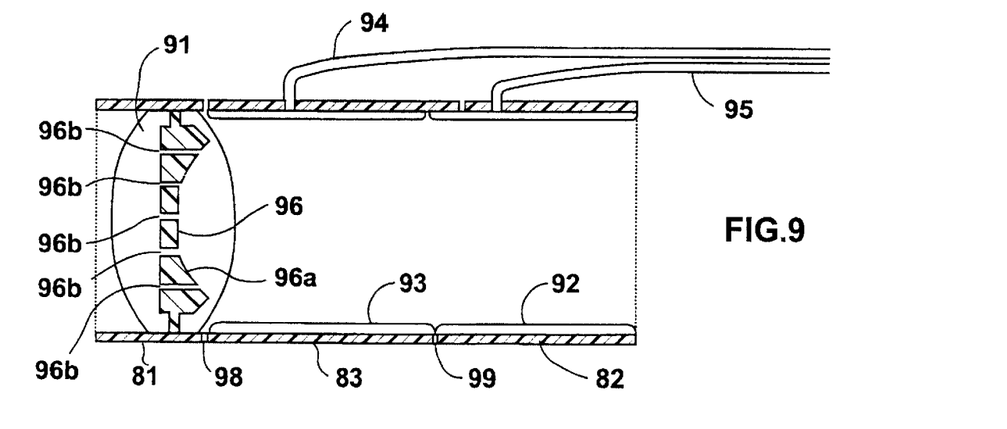
FIG. 9 illustrates a further probe constructed in accordance with the present invention.
Figure 10:
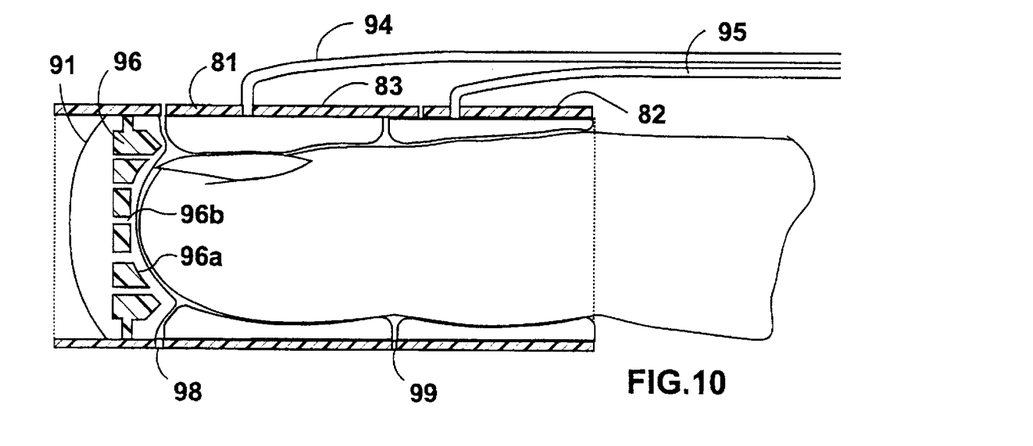
FIG. 10 illustrates the probe of FIG. 9 as applied to a patient's finger.

The Devices of FIGS. 8–10

FIGS. 8–10 illustrate probes wherein the distal end section, therein designated 81, of the housing is an open cylinder rather than closed (e.g., of thimble shape) as described above; in addition, the open cylinder is closed by the end fluid chamber 91 mounted within and closing the distal end of the cylinder. Thus, the end fluid chamber 91 is exposed on its outer side to the atmosphere. Such an arrangement equalizes the pressure applied to the distal tip of the patient's finger.

Replacing the front-most segment (which is situated mainly in front of the finger tip) by the open cylinder 81 closed at its outer end by the fluid filled elastic bag 91, which is open to the atmosphere at its front, exploits the advantages of the Laplace effect (constant pressure over a wide range of volume changes), and removes the need for supplying pressure to a third compartment, as described in our previous Application No. 124787, filed Jun. 7, 1998.

The proximal end section 82 and the intermediate section 83, of the housing, together with their respective fluid chambers 92 and 93, are of the same construction as described above.

FIGS. 9 and 10 illustrate a modification in the probe construction of FIG. 8, wherein the end fluid chamber 91, closing the distal end section 81 of the housing as described above, is provided with a rigid element 96. This element is secured to the open end of housing section 81 and is enclosed by the membrane defining the end fluid chamber 91. The side of rigid element 96 facing the patient's finger, when received within the probe, is of a concave configuration, as shown at 96a, for receiving the patient's finger. In addition, rigid element 96 is formed with a plurality of through-going holes 96b permitting the free flow of the fluid within the end chamber 91 with respect to both sides of this element.

The probe illustrated in FIGS. 9 and 10 further includes air vents 98 between the distal end section 81 and the intermediate section 83 of the housing, and further vents 99 between the proximal end section 82 and the intermediate section 83 of the housing, as described above with respect to FIGS. 6 and 7.

As seen in FIG. 10, most of the end fluid chamber 91 in the closed distal end section 81 is forwardly of the distal tip of the patient's finger, with little of that chamber enveloping the finger, as described above with respect to end fluid chamber 91 in FIG. 7.

According to preliminary tests, it appears that the preferred overall length of the housing in the foregoing constructions is about 50 mm, sufficient to cover the first two phalanges of a patient's finger. In a tested construction, the distal section was 12 mm, the middle end section was 23 mm, and the proximal section was 15 mm. As indicated above, best results were found when the middle section, containing the sensor, is longer than each of the two end sections.

Other Variations (FIGS. 11–14)

In the above described constructions, preferably the middle section of the probe serves as the sensing site, and the two end sections serve to buffer the sensing site against venous shock waves and retrograde venous back-flow, to prevent venous pooling, and also to extend the pressure field to the extreme tip of the finger, as in some of the constructions described in Publication WO98/04182.

Figure 11:
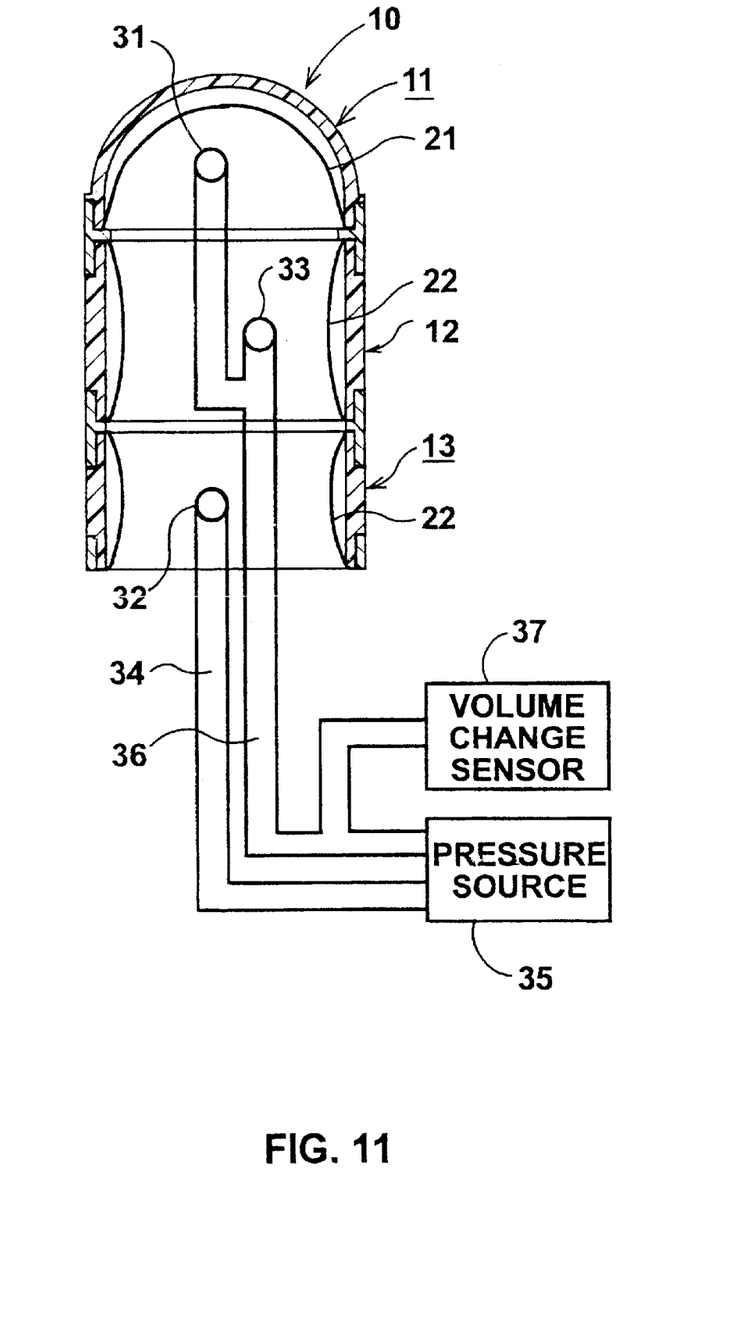
FIG. 11 illustrates a modification in the probe of FIG. 1.

FIG. 11 illustrates a variation in the construction of the probe of FIG. 1, wherein both the distal segment 11 and the middle segment 12 are used as the sensing sites. In all other respects, the probe in FIG. 11 is constructed and operates in the same manner as described above with respect to FIG. 1.

The inner rings, 42, 43, and 44, as described above with respect to FIG. 4, may also be used in the three-part housing constructions described in the other drawing figures. It will also be appreciated that the above-described constructions could include more than one middle part.

As also described in WO98/04182, the collective effect of the uniform pressure field in the new designs illustrated herein also partially unloads arterial wall tension to maximize arterial wall motion. The U-bar 24 could be mounted to the housing to span also the middle section, and even also the proximal end section. Also, the spaces within the housing between the chambers can be vented to the atmosphere, e.g., by providing holes through the connecting rings 14 and 15 in FIGS. 1–3, and in the corresponding portions of the housing 40 in FIGS. 4 and 5. It will also be appreciated that the sensor used with the probes described herein could be of any of the types, including the optical Hall effect, ultra sound, etc. type, e.g., as described in Publication WO98/04182.

Figure 12:
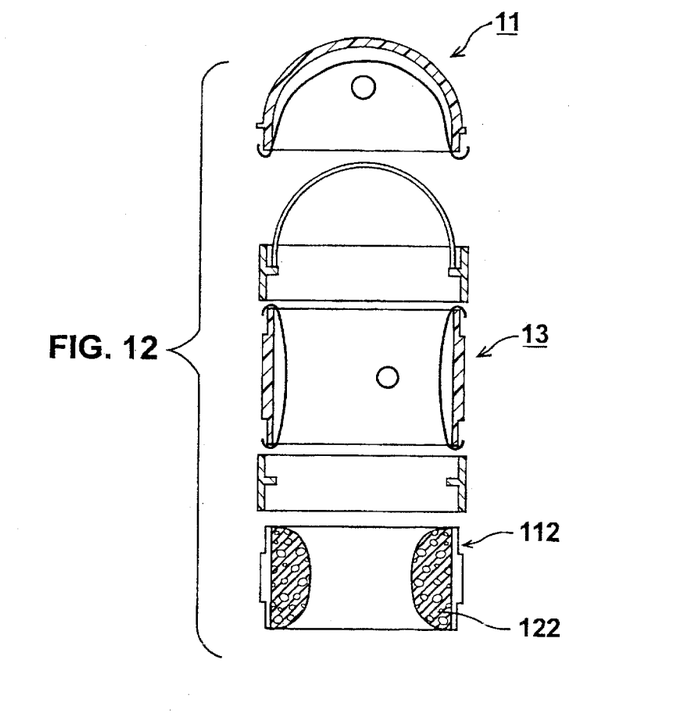
FIGS. 12 and 13 illustrate two further constructions including a sponge cushion in the proximal end section, rather than a pressurized chamber.
Figure 13:
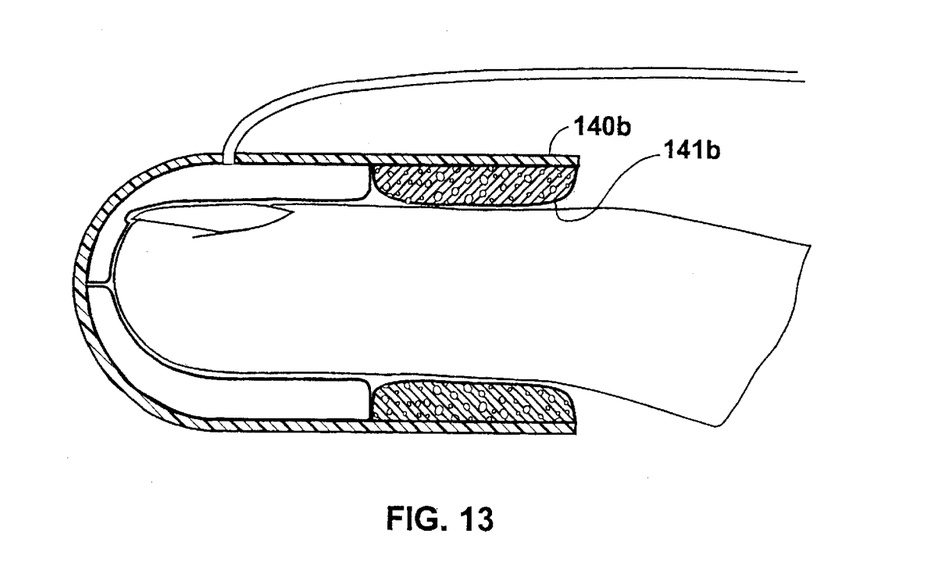

FIGS. 12 and 13 illustrate two further variations, wherein the proximal end section of the housing includes a sponge cushion, rather than a pressurized chamber. Thus, FIG. 12 illustrates a construction similar to that of FIG. 2, except that the proximal end section 112 of the housing includes a sponge cushion 122, and therefore does not include the connection (opening 32, FIG. 2) to a pressurized source. The remaining construction of the probe is the same as described above with respect to FIG. 2, and therefore the same parts carry the same reference numerals.

FIG. 13 illustrates a construction somewhat similar to that of FIG. 7, wherein the proximal end section 162 is similarly provided with a sponge cushion 172, rather than a connection to the pressure source. The sponge cushions 122 of FIG. 12 and 172 of FIG. 13 could be of sponge rubber or the like.

Figure 14:
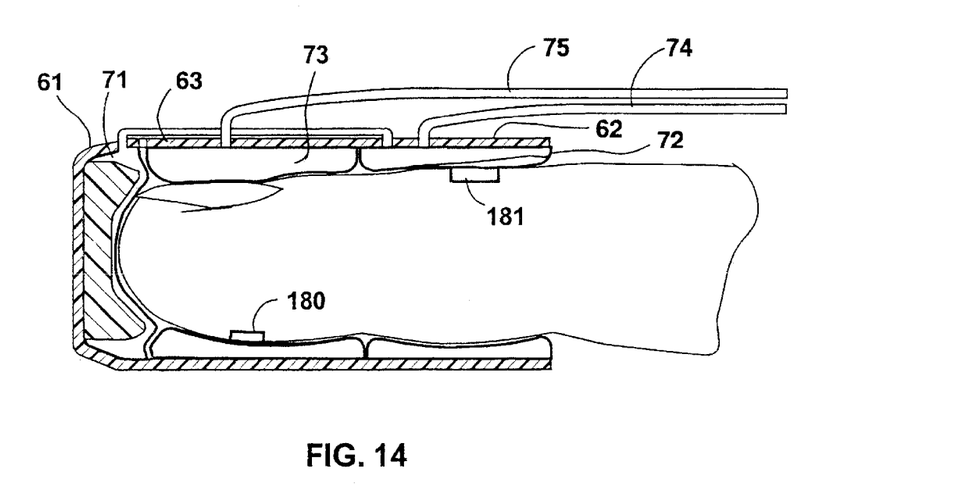
FIG. 14 illustrates a still further construction including two optical sensors within the finger probe.

FIG. 14 illustrates a probe construction similar to that of FIGS. 6 and 7, except that the probe includes an optical sensor 180, 181, in the middle section 63 and in the proximal end section 62, respectively. Thus, optical sensor 180 is oriented to measure volume changes from the underside of the finger where a high proportion of the blood vessels are so called arteriovenous anastomoses (AVA), while optical sensor 181 is oriented to measure volume changes from the upper side of the middle phalange of the finger for identiying and characterizing blood flow characteristics where a low portion of the blood vessels are AVA. Either or both optical sensors may be used independently or in contact with the volume change measurement.

It will be appreciated that the probes described herein may be used for all the applications described in the above-cited WO98/041824, incorporated herein by reference, including measuring blood pressure, as well as in the applications described in PCT/IL99/00292, also incorporated herein by reference.

Many other variations, modifications and applications of the invention will be apparent.

What is claimed is:

1. A device for application to a body part of a patient to determine the physiological condition of the patient, comprising:
   a housing for receiving the body part;
   pressurizing means for applying a pressure field around the body part when received in said housing;
   and a sensor for sensing changes in said body part related to changes in blood volume therein, wherein
   said housing includes at least three contiguous but separate sections including a distal end section at a distal end of said housing, a proximal end section at a proximal end of said housing, and at least one middle section between said distal and proximal end sections,
   and wherein said pressurizing means applies a pressure field to portions of the body part received within at least said distal end section and said middle section of the housing,
   and said sensor senses changes in the portion of said body part received within said middle section of the housing.

2. The device according to claim 1, wherein said pressurizing means also applies a pressure field to said proximal end section.

3. The device according to claim 2, wherein said pressurizing means comprises:
   a deformable membrane within said housing defining end fluid chambers with said distal and proximal end sections, and a middle fluid chamber with said middle housing section;
   and a fluid pressure source for applying a fluid pressure to all of said chambers.

4. The device according to claim 3, wherein said deformable membrane comprises resilient elastomeric material.

5. The device according to claim 3, wherein said distal and proximal middle section is longer than said housing end sections.

6. The device according to claim 3, wherein said housing is configured to receive a digit of the patient;
   said distal end section being closed and enclosing one or more chambers, for receiving a distal end of the digit;
   said proximal end section being open and enclosing one or more additional chambers, at the proximal end of the housing and connected thereto by said middle section.

7. The device according to claim 6, wherein said sensor also senses changes in the distal end of the digit received in said distal end of the housing.

8. The device according to claim 6, wherein said housing comprises at least three contiguous parts secured together, including:
   a thimble-shaped cap at the closed distal end of the housing;
   an annular collar at the proximal end of the housing; and
   an intermediate sleeve secured between the thimble-shaped cap and the annular collar.

9. The device according to claim 8, wherein said parts of the housing are secured together by a first annular ring which secures said thimble-shaped cap to said intermediate sleeve, and a second annular ring which secures said intermediate sleeve to said annular collar.

10. The device according to claim 9 wherein, on said first annular ring, is mounted a U-shaped bar pressing said membrane means against the inner surface of said thimble-shaped cap to divide the chamber therein into two sub-chambers to be located on opposite sides of a distal tip of the digit when inserted into said housing, and to more firmly retain the digit therein.

11. The device according to claim 9, wherein said deformable membrane includes at least three separate membranes, comprising:
   a distal membrane having an open end secured by said first annular ring to said thimble-shaped cap to define one end chamber in said cap;
   an annular intermediate membrane having open opposite ends secured to said intermediate sleeve by said first and second annular rings to define a middle chamber in the intermediate sleeve;
   and a further annular membrane having one end secured to said annular collar by said second annular ring, and the opposite end secured to said annular collar by a third annular ring to define another end chamber within said annular collar.

12. The device according to claim 3, wherein said membrane means consists of a single membrane of tubular shape closed at one end and open at an opposite end, said device further including a plurality of spaced internal annular rings for clamping spaced annular portions of said membrane to an inner surface of said housing to define said fluid chambers.

13. The device according to claim 12, wherein the inner surface of said tubular housing, and outer surfaces of said spaced internal annular rings, are formed with mating rib and recess formations enabling the rings to be snap-fitted within said housing, and to press the annular portions of the tubular membrane against the inner surface of the housing to define said chambers.

14. The device according to claim 13, wherein said mating rib and recess formations comprises annular ribs formed on the inner surface of said housing, and annular recesses formed on the outer surfaces of said rings.

15. The device according to claim 12, wherein said housing comprises one part of tubular shape closed at said distal end and open at said proximal end.

16. The device according to claim 12, wherein, on one of the internal annular rings at the distal end of the housing is mounted a U-shaped bar pressing said membrane means against a thimble-shaped cap to divide a first chamber therein into two sub-chambers to be located on opposite sides of a distal tip of a patient's digit when inserted into said housing, and to more firmly retain the patient's digit therein.

17. The device according to claim 6, wherein said closed distal end of the housing, and the end fluid chamber therein, are of substantially shorter length than the other housing sections and the fluid chambers therein.

18. The device according to claim 6, wherein said end fluid chamber in the closed distal end section of the housing includes an abutment element having a concave surface for receiving the distal tip of the patient's digit.

19. The device according to claim 18, wherein said abutment element is located such that, when engaged by the distal tip of the patient's digit, most of said end fluid chamber is located forwardly of the distal tip of the patient's finger.

20. The device according to claim 6, wherein said end chamber in the closed distal end section of the housing is fluidly coupled to the fluid chamber in the open proximal end section of the housing.

21. The device according to claim 6, wherein said distal end section of the housing is an open cylinder and is closed by the end fluid chamber therein mounted within and closing one end of the cylinder.

22. The device according to claim 21, wherein said end fluid chamber closing the open end of the cylinder includes a rigid element mounted within one end of the cylinder and enclosed by the membrane defining said end fluid chamber.

23. The device according to claim 22, wherein said rigid element is formed with holes therethrough permitting free flow of fluid within said end chamber with respect to both sides of the rigid element.

24. The device according to claim 23, wherein said rigid element is formed with a concave surface for receiving the distal tip of the patient's finger.

25. The device according to claim 21, wherein said end fluid chamber closing the end of said open cylinder is open to the atmosphere at a front thereof to provide relatively constant pressure over a wide range of volume changes in accordance with the Laplace effect.

26. The device according to claim 1, wherein said pressurizing means applies a static pressure field of sufficient magnitude such that a heartward-most compartment of said pressure field acts as a venous tourniquet to prevent venous pooling, and retrograde venous blood flow or shockwave propagation into the more distal end of the body part.

27. The device according to claim 1, wherein said proximal end section includes a sponge cushion.

28. The device according to claim 1, wherein said sensor includes an optical sensor at an underside of said middle housing section, and another optical sensor at an upper side of said proximal end section.

29. The device according to claim 1, wherein said housing sections further include air vents between said sections venting an interior of the housing to atmosphere.

30. The device according to claim 1, wherein said housing sections are of a total length to cover two phalanges of a patient's finger.

31. The device according to claim 1, wherein said housing sections are of a total length of approximately 50 mm.

* * * * *